(12) United States Patent
Olson et al.

(10) Patent No.: US 8,282,620 B2
(45) Date of Patent: Oct. 9, 2012

(54) CONTAINER FOR PUMP SYSTEM

(75) Inventors: James M. Olson, Plymouth, MN (US); Michael Hegland, Mounds View, MN (US); Dale F. Seeley, Spring Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 733 days.

(21) Appl. No.: 12/366,165

(22) Filed: Feb. 5, 2009

(65) Prior Publication Data

US 2010/0198184 A1    Aug. 5, 2010

(51) Int. Cl.
*A61B 19/00* (2006.01)
*B65B 1/04* (2006.01)
*B65B 3/04* (2006.01)

(52) U.S. Cl. ............... 604/408; 604/403; 141/10
(58) Field of Classification Search ...... 604/8, 403–416; 222/207–214, 102, 107; 417/472, 479; 141/10
See application file for complete search history.

(56) References Cited

U.S. PATENT DOCUMENTS

| | | | |
|---|---|---|---|
| 4,386,929 A | 6/1983 | Peery | |
| 5,061,243 A | 10/1991 | Winchell | |
| 5,743,878 A | 4/1998 | Ross | |
| 6,086,560 A | 7/2000 | Kriesel | |
| 6,276,567 B1 * | 8/2001 | Diaz et al. | 222/81 |
| 7,000,806 B2 | 2/2006 | Py | |
| 7,188,749 B2 | 3/2007 | Miller | |
| 7,850,051 B2 * | 12/2010 | Py et al. | 222/207 |
| 2004/0143235 A1 * | 7/2004 | Freund et al. | 604/408 |
| 2007/0106218 A1 | 5/2007 | Yodfat | |
| 2008/0119707 A1 | 5/2008 | Stafford | |

* cited by examiner

*Primary Examiner* — Philip R Wiest (57) ABSTRACT

A container for housing a fluid therapeutic composition includes a rigid housing, a collapsible bag and a seal. The housing has an opening and an interior surface. The interior surface forms a cavity having a volume. The bag is disposed in the housing and is expandable to contact the interior surface of the housing and occupy the entire volume of the cavity when filled with the fluid therapeutic composition. The bag has an opening that is fixed in proximity to the opening of the housing. The seal is configured to prevent air from entering the bag via the bag opening and to prevent air from entering the cavity of the housing via the housing opening.

13 Claims, 9 Drawing Sheets

CONTAINER FOR PUMP SYSTEM

FIELD

This disclosure relates, inter alia, to containers for holding therapeutic fluid and pump systems and methods including such containers. More particularly, this disclosure relates containers having rigid housings and flexible bags disposed in the housings for retaining therapeutic fluid.

BACKGROUND

A variety of pump systems are employed for delivering therapeutic fluid to a patient. Such systems typically employ reservoirs having rigid surfaces, such as a metal bellows or a glass vial with a moving plunger or syringe. Such reservoirs or associated accessory components, such as an actuator, can be expensive to manufacture, and thus are not ideal for a low cost or disposable pump. For example, systems with rigid vials employing a piston to pump fluid from the vial must have sufficiently powerful motors or actuation mechanisms to overcome stiction and negative pressures associated with dispense in such systems, but should also be finely tailored to deliver precise amounts of therapeutic fluid. Systems with such powerful and precise electrical and mechanical components can be expensive to manufacture.

Some pump systems employ conformable reservoirs or flexible bags, e.g. bladders, which may be amenable to lower manufacturing costs. Unlike rigid vials, flexible bags allow for neutral pressure dispense or positive pressure dispense, if the bag is elastomeric. Accordingly, more energy efficient and lower cost pumping mechanisms or flow control mechanisms may be employed with conformable reservoir systems relative to rigid vial pump systems. However, such conformable reservoirs lack the mechanical protection afforded by rigid reservoirs. In addition, the costs associated with handling and filing conformable reservoirs tend to be higher than their rigid counterparts or require difficult filling procedures to be carried out by the end user. Further, conformable reservoirs tend to suffer from drawbacks associated with the ability of molecules to cross the material of the reservoir. Such drawbacks include permeation loss of one or more component of the therapeutic fluid or ingress of unwanted molecules into the therapeutic fluid. Permeation can significantly reduce shelf life of therapeutic fluids stored in conformable bladders relative to rigid counterparts.

Some therapeutic fluids, such as those containing insulin are often stored for years prior to being administered to a patient. Accordingly, permeation issues can present significant challenges for storage and subsequent delivery of such therapeutic fluids via pump systems in a cost effective manner.

SUMMARY

The present disclosure describes, inter alia, systems, devices, and methods that employ reservoirs or containers having a collapsible bag disposed within a rigid housing. Such reservoirs or containers may be configured for use in pump systems and share the benefits of rigid containers and flexible containers while eliminating some of the drawbacks. For example, such containers combine the low permeation and ease of handling and filling qualities of rigid containers and the lower cost possibilities of pump systems that employ conformable reservoirs.

In an embodiment, a container for housing a fluid therapeutic composition includes a rigid housing, a collapsible bag and a seal. The housing has an opening and an interior surface. The interior surface forms a cavity having a volume. The opening is in fluid communication with the cavity. The collapsible bag is configured to contain the fluid therapeutic composition. The bag is disposed in the housing and is expandable to contact the entire interior surface of the housing such that the bag and its contents occupy the entire volume of the cavity. The bag has an opening to allow the therapeutic agent to be introduced into, or exit from, the bag. The opening of the bag is fixed in proximity to the opening of the housing. The seal is configured to prevent air from entering the bag via the bag opening and to prevent air from entering the cavity of the housing via the housing opening. The seal may include a metallic foil layer disposed across the housing opening and may include a pierceable and resealable septum configured to allow fluid to be introduced into, or withdrawn from, the bag.

In various embodiments, the bag may be elastomeric and have an unstressed internal volume of near zero so that when filled the bag maintains a positive pressure. In some embodiments, the bag has an expanded, unstressed volume that is equal to or greater than the volume of the cavity of the housing, where the bag maintains a neutral pressure throughout dispense of the therapeutic fluid.

In various embodiments, a container as described above is incorporatable into an infusion system. The infusion system may have a cannula configured to pierce the seal of the container to access to the therapeutic fluid contained in the bag. The infusion system may also include a drive mechanism or flow restrictor, depending in part on whether the bag is configured for positive or neutral pressure dispense, to control the rate at which the therapeutic fluid is delivered to a patient from the container.

By providing containers having a collapsible bag disposed within a rigid housing, and infusion systems employing such containers, permeation issues may be reduced and cost effective pump systems may be made. For example, disposing the bag in the rigid housing provides the benefits of reduced permeation, ease of handling and filling, and protection associated with the rigid housing. In addition, use of a bag can provide neutral pressure or positive pressure, if the bag is elastomeric, throughout dispense. Neutral or positive pressure, as opposed to negative pressure associated with some rigid vial dispensing systems, allows less expensive or less complicated drive mechanisms to be employed. These and other advantages will be readily understood from the following detailed descriptions when read in conjunction with the accompanying drawings.

The drawings are not necessarily to scale. Like numbers used in the figures refer to like components, steps, etc. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

The present disclosure describes, inter alia, systems, devices, and methods that employ a container having a collapsible bag disposed in a rigid housing. By disposing the collapsible bag in a rigid housing, such as a vial, high speed filling lines may be accommodated and a hermetic barrier for agent preservation may be provided. The rigid housing may also serve to protect the collapsible bag and its contents and may be configured for ready insertion in, removal from, or incorporation into an infusion system. In some embodiments, the collapsible bag is configured to maintain neutral pressures during dispense; e.g., when the unstressed size of the bag equals or is greater than the volume defined by the rigid housing. In such embodiments, an on-demand vent may be included in the rigid housing to allow the neutral pressure dispense. Such an on-demand vent would not be practicable without the inclusion of the inner collapsible bag due to contamination issues, permeation issues, or the like. In some embodiments, the collapsible bag is configured to maintain slight positive pressure during dispense; e.g., when the unstressed volume of the bag is near zero.

By providing a neutral or positive pressure reservoir, such containers may be included in low cost infusion systems that do not require elaborate or expensive drive mechanism components. Of course, the containers described herein may be used with or incorporated into any suitable infusion system, regardless of the cost or complexity of the system. In various embodiments, a container, as described herein, may be used with or incorporated into a fully implantable infusion system. In some embodiments, a container, as described herein, may be used with or incorporated into a partially or non-implantable infusion system. In some embodiments, a container, as described herein, may be used with or incorporated into a patch-type transdermal infusion system. Any suitable drive mechanism may be employed for infusing fluid from the reservoir to a patient. Examples of suitable drive mechanisms include piston pumps, syringe or plunger-type drive mechanisms, spring or elastomeric forces, peristaltic pumps, or the like.

Figure 11:
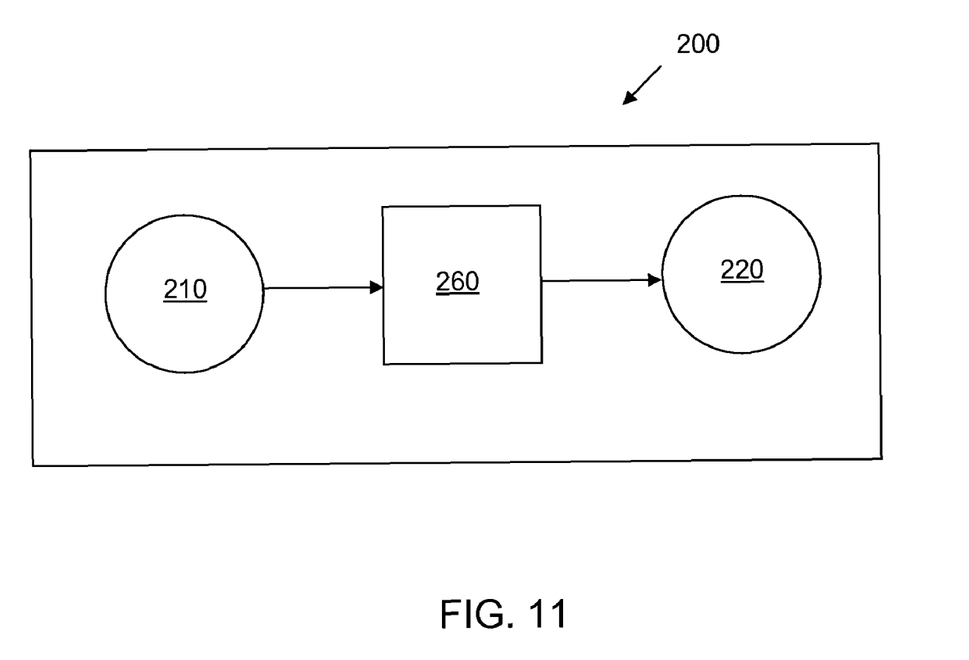
FIG. 11 is a schematic block diagram of a representative embodiment of an infusion system employing a flow restrictor.

Various aspects and embodiments of containers or portions thereof are depicted in FIGS. 1-8. Various aspects and embodiments of infusion systems including containers as reservoirs are depicted in FIGS. 9-11.

Referring now to FIGS. 1-5, schematic longitudinal cross sections of representative containers 100, or portions thereof, for holding therapeutic fluid are shown. The containers 100 depicted in FIGS. 1-4 include a rigid housing 10 and a collapsible bag 20 disposed in the housing 10. The rigid housing 10 has an interior surface 12 defining a cavity 14 having a volume (see, e.g. FIG. 5). The housing 10 forms an opening 16 in fluid communication with the cavity 14. The bag 20 has an external surface 21 and an internal surface 22. The internal surface 22 defines a variable volume chamber 24. As the bag 20 expands, the volume of the chamber 24 increases. Expansion of the bag 20 is limited by the volume of the cavity 14 of the rigid housing 10. Thus, when disposed in the housing 10, the maximum expanded volume of the chamber 24 of the bag 20 is about the same as the volume of the cavity 14 of the housing.

Figure 1:
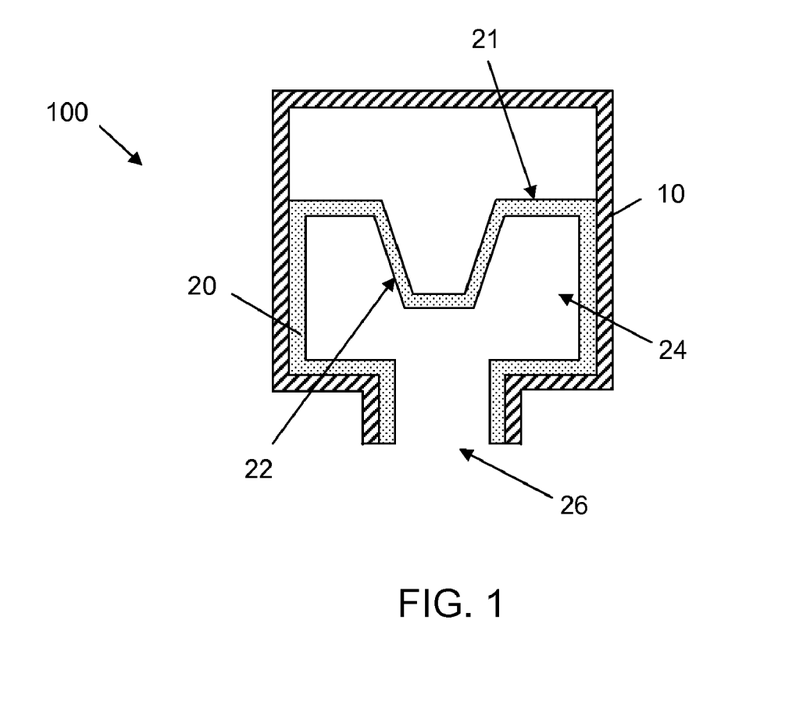
FIGS. 1-2 are schematic cross-sectional views of representative embodiments of containers including a bag disposed within a rigid housing.

In various embodiments, the bag 20 has an expanded, unstressed size that is equal to or greater than the volume of the cavity 14 of the housing 10. In such embodiments, the fluid pressure in the bag 20 remains substantially neutral as the volume of the chamber 24 of the bag 20 contracts as therapeutic fluid is dispensed, provided that the pressure in the cavity 14 of the housing 10 remains neutral. An example of a bag 20 having an expanded, unstressed size that is equal to or greater than the volume of the cavity 14 of the housing 10 is shown in FIG. 1 in a partially empty state. Of course, in certain circumstances a bag having an unstressed, expanded volume less that the volume of the volume of the cavity of the housing may be used. In such circumstances, it may be desirable to evacuate air from the remaining volume of the cavity or introduce an inert (relative to the therapeutic fluid) gas or material into the unoccupied volume of the cavity.

Figure 2:
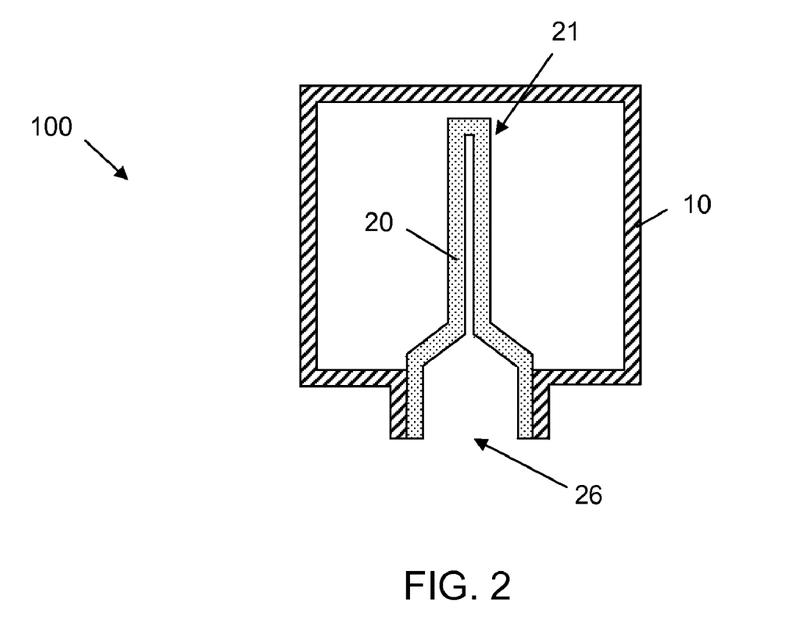

In various embodiments, the bag 20 is elastomeric and is configured to maintain slight positive pressure during dispense. In some embodiments, the bag 20 has an unstressed internal volume of near zero. In such embodiments, the bag 20 is formed from elastomeric materials. The bag 20 is biased towards the empty state and tends to expel fluid from an expanded chamber 24. The more the bag 20 is expanded, the greater the pressure in the chamber 24. In such embodiments, the bag 20 maintains slight positive pressure during dispense of therapeutic fluid from the bag. An example of a bag 20 having an unstressed volume of near zero is depicted in FIG. 2 in a substantially empty state.

Figure 3:
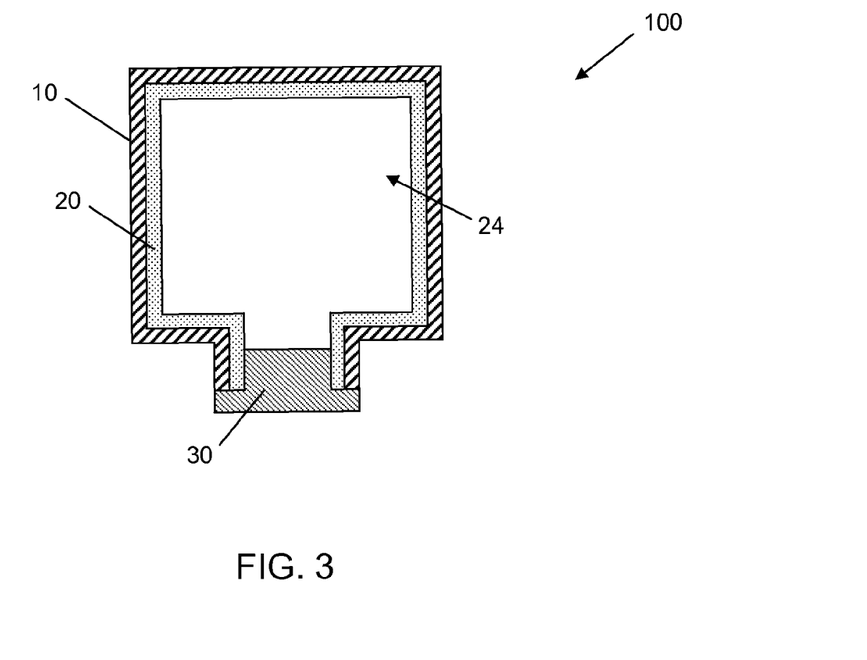
FIGS. 3-4 are schematic cross-sectional views of representative embodiments of sealed containers including a bag disposed within a rigid housing.
Figure 4:
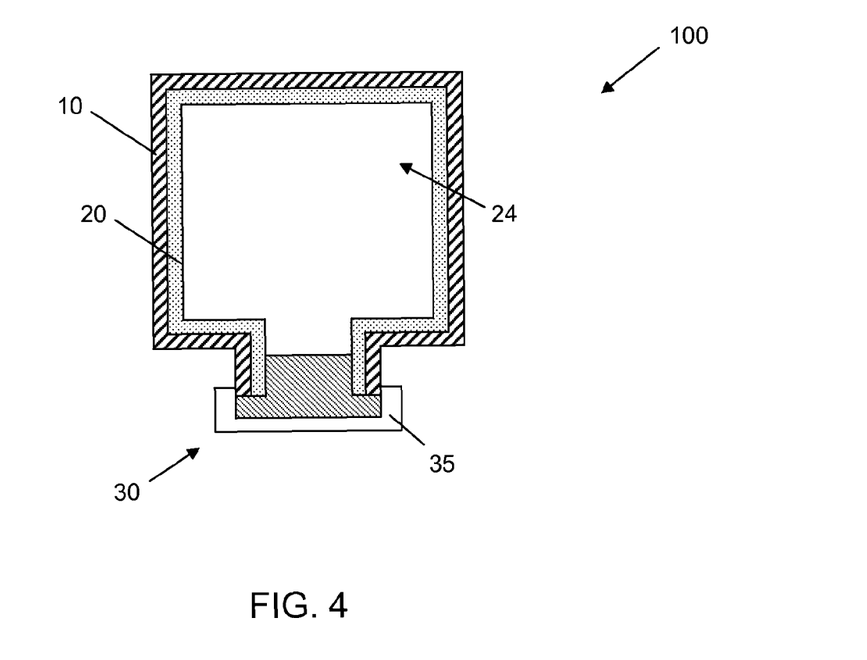
Figure 5:
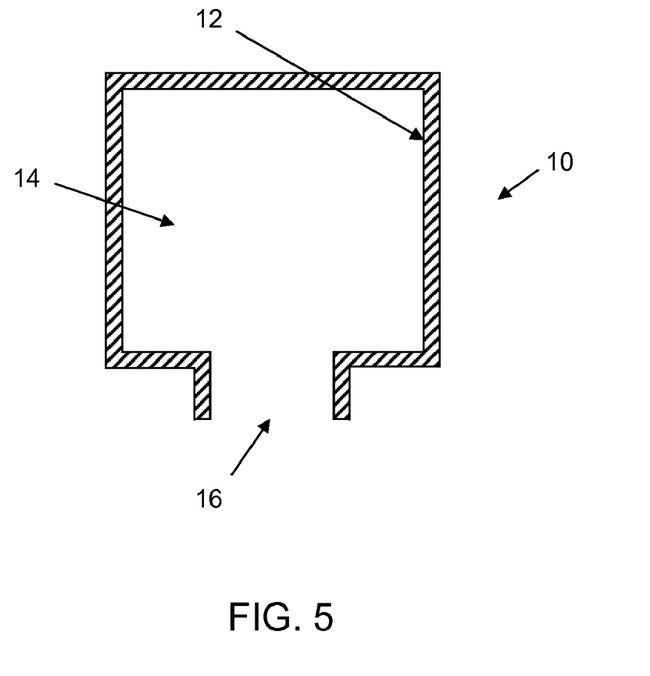
FIG. 5 is a schematic cross-sectional view of a representative embodiment of a rigid housing of a container.
Figure 6:
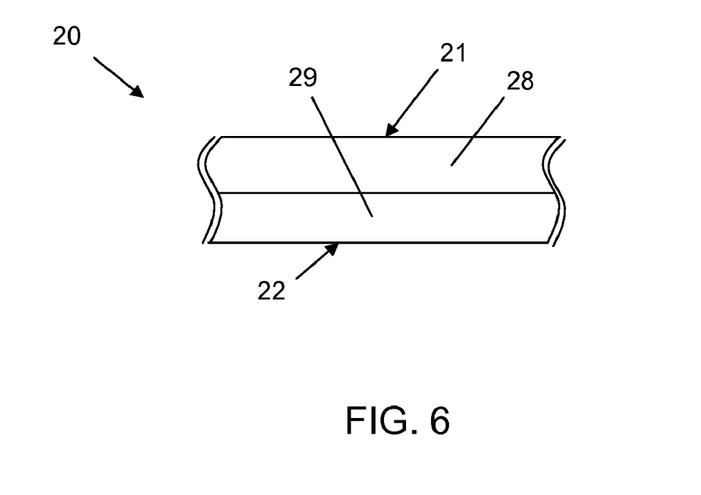
FIG. 6 is a schematic cross-sectional view of a representative embodiment of a coated bag that may be included in various embodiments of containers.
Figure 7:
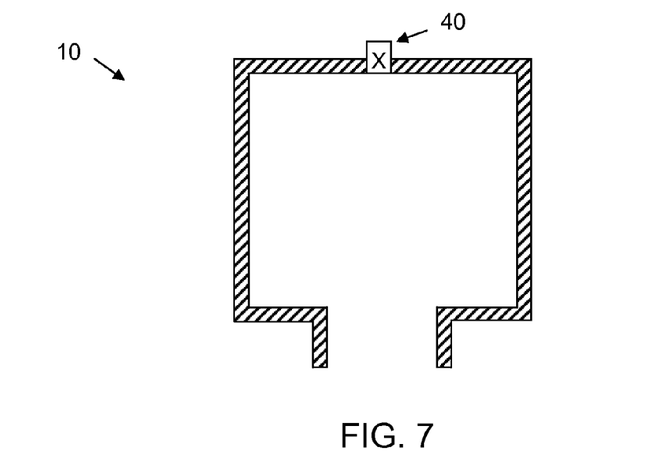
FIG. 7 is a schematic cross-sectional view of a representative embodiment of a rigid housing of a container having a vent, which is shown in block form.

Regardless of whether the bag 20 has an expanded, unstressed size that is equal to or greater than the volume of the cavity 14 of the housing 10 or has an unstressed volume of near zero, the bag 20 is expandable when filled with a fluid therapeutic composition such that the outer surface 11 contacts the entire interior surface of the housing 10 and the bag and therapeutic fluid occupy the entire volume of the cavity of the housing 10, e.g. as shown in FIGS. 3-4. It will be understood that based on the shape of the housing 10 and the shape and properties of the bag 20, there may be some volume or volumes of the cavity of the housing 10 that are not occupied by the bag 20 when the bag is filled (within the confines of the housing) with therapeutic fluid. However, for the purposes of the present disclosure, the bag and its contents will be considered to occupy the entire volume of the cavity when such minor volumes are not occupied. Similarly, for the purposes of the present disclosure, it will be understood that the outer surface of the bag will be considered to contact the entire inner surface of the housing when there are some areas of the inner surface that are not contacted due to the shape and properties of the bag relative to the shape of the housing.

A rigid housing 10 may formed of any suitable material capable of maintaining its shape and form under typical storage conditions for containers holding therapeutic fluid. Preferably, the material and thickness of the housing 10 prevents ready permeation of air or components of a therapeutic fluid through the material of housing 10. For example and in various embodiments, the housing 10 is formed from material of suitable dimensions to prevent significant permeation of phenol if phenol were contained in the housing as a preservative of a therapeutic fluid. By way of example, the housing 10 may be configured to prevent permeation of the phenol such that a sufficient amount of phenol for purposes of preservation remains in the therapeutic fluid after two years of storage at room temperature in the housing. In various embodiments, the housing 10 is formed from metallic material, such as stainless steel, titanium or the like; silica-containing material, such as glass; impermeable polymeric material, or the like. In addition to the nature of the material selected, it will be understood that the rigidity and permeability of the housing can be varied based on the thickness of the housing, and other factors known to those of skill in the art. For some materials, such as metals and glass materials, nearly any thickness should be sufficient for preventing permeation.

A housing 10 may be in any suitable shape. When used as reservoirs of pump systems, e.g. as described below with regard to FIGS. 8-11, a container 100, whose outer dimensions are defined by housing 10, may be configured to be readily incorporated into, and in some embodiments removable from, such a system. Such containers may, in some embodiments, be readily exchanged to replenish the supply of therapeutic agent in the pump system. In some embodiments, a container 100 is in the shape of, or takes the form of, a glass vial suitable for use in automated filling equipment for dispensing therapeutic fluid into such vials.

A bag 20 may be formed from any suitable material. In various embodiments, the bag is formed from a thin polymeric material or a metallic foil. Examples of polymeric materials that may be used to form a suitable bag include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. Any suitable elastomer such as silicone or urethane containing polymers may be used. Whether the bag 10 exhibits elastic properties and is biased towards the empty state or is unstressed in a filled state (within the confines of the housing) will depend, in part, on the material selected. One skilled in the art will understand which materials to select or fabricate to impart desired properties on the bag 20. It will be further understood that the particular type or types of material forming the bag may be selected based on whether the materials are compatible with the materials included in the therapeutic fluid to be housed in the bag 10.

The bag may be formed through heat sealing, laser welding, sonic welding, application of adhesive, extruding, or any other method know in the art of bag or balloon making. Because the bag 20 is disposed within a relatively impermeable housing 10, the bag 10 may be somewhat permeable to air or components of the therapeutic fluid. Of course, the bag 10 may be relatively impermeable. However, it should be noted that significant permeation can often occur through seals employed to form the bag. Accordingly, even if the bulk material of the bag is impermeable, permeation may occur through a seal. Such issues of permeation are significantly reduced by disposing the bag 20 with an impermeable housing 10.

Preferably, the bag is formed from material that is compatible with therapeutic fluid that it is intended to contain. Alternatively or in addition, and with reference to FIG. 6, the bag 20 may include an interior coating 29 that is compatible with the therapeutic fluid. The compatible coating 29 may serve as the inner surface 22 of the bag 20 that the therapeutic contacts and may provide a barrier between the therapeutic fluid and the bulk material layer 28 of the bag 20. In addition or alternatively, coating 29 may serve to decrease the permeability of the bag 20, allowing for longer term storage of therapeutic fluid in the bag. Alternatively, a coating, such as a metalized layer, may be applied to the exterior surface of the bag to decrease permeability (e.g. if 28 were the coating layer and 29 were the bulk material layer of the portion of the bag 20 depicted FIG. 6). Any suitable coating 29 may be employed, and the coating 29 may be applied via any suitable technique before or after the bag is formed.

Referring back to FIGS. 1-2, a portion of the bag 20 in proximity to the bag opening 26 may be fixed relative to the housing 10 in proximity to the opening of the housing. The bag 10 may be fixed to the housing with adhesive, laser welding, or via any other suitable technique.

As shown in FIGS. 3-4, the container 100 may include a seal 30 or plug, such as a stopper or self-sealing septum configured to prevent air from entering the chamber 24 of the bag 20 via the bag opening and to prevent air from entering the cavity of the housing 10 via the opening of the housing. It will be understood that some air may enter the chamber of the bag or the cavity of the housing through or around a seal configured to prevent such air flow. In some embodiments, the seal 30 is used to fix the position of the opening of the bag 20 relative to the opening of the housing 20 by pressing the bag against the housing. The seal 30 may include, or be formed entirely from, a metallic foil layer 35 that may be bonded, sealed, adhered, or the like to the housing 10. The seal 30 or its components, such as a stopper, septum and foil, may be readily placed on container 100 through the use of automated filling equipment; e.g., when the container 100 is the form or shape of a glass vial. When sealed, the container 100 provides a relatively impermeable barrier between therapeutic fluid disposed within the chamber 24 of the bag 20 and the environment outside the housing 10.

However, when the container 100 is hermetically sealed, dispensing therapeutic fluid contained in the bag 20 may create a vacuum in the cavity of the housing 10 as the fluid dispenses, particularly if fluid is dispensed through a fine gauge cannula (e.g., as described below with regard to FIGS. 9A-B). Further, if such containers 100 are to be employed in pump systems employing certain drive mechanisms, it may be desirable to maintain neutral or slight positive pressure of the fluid in the bag 10. By way of example, some peristaltic drive mechanisms are not able to draw fluid against a negative pressure. Accordingly and with reference to FIG. 7, a vent 40 may be included in the housing 10. In order to maintain a hermetic seal within the housing 10 until the fluid is to be dispensed, it may be desirable for the vent 40 to be an on-demand vent or an actuatable vent. Any suitable vent 40 may be employed and any suitable mechanism for actuating the vent 40 may be employed.

Figure 8A:
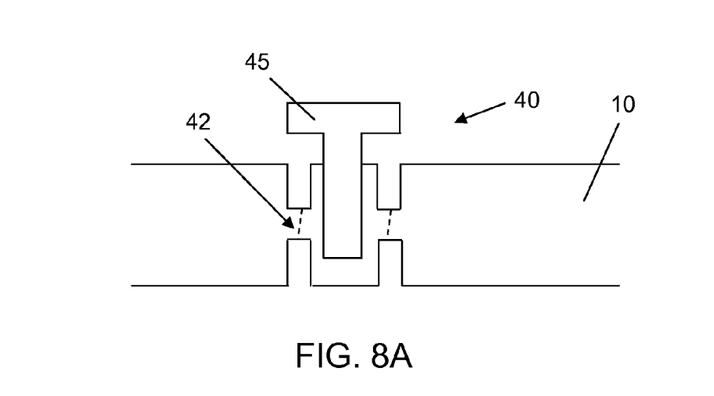
FIGS. 8A-B are schematic cross-sectional views of an embodiment of an acuatable vent mechanism incorporated into a housing of a container.
Figure 8B:
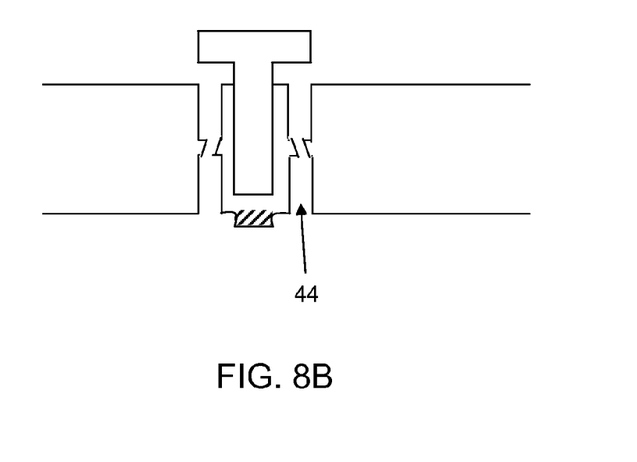
Figure 9A:
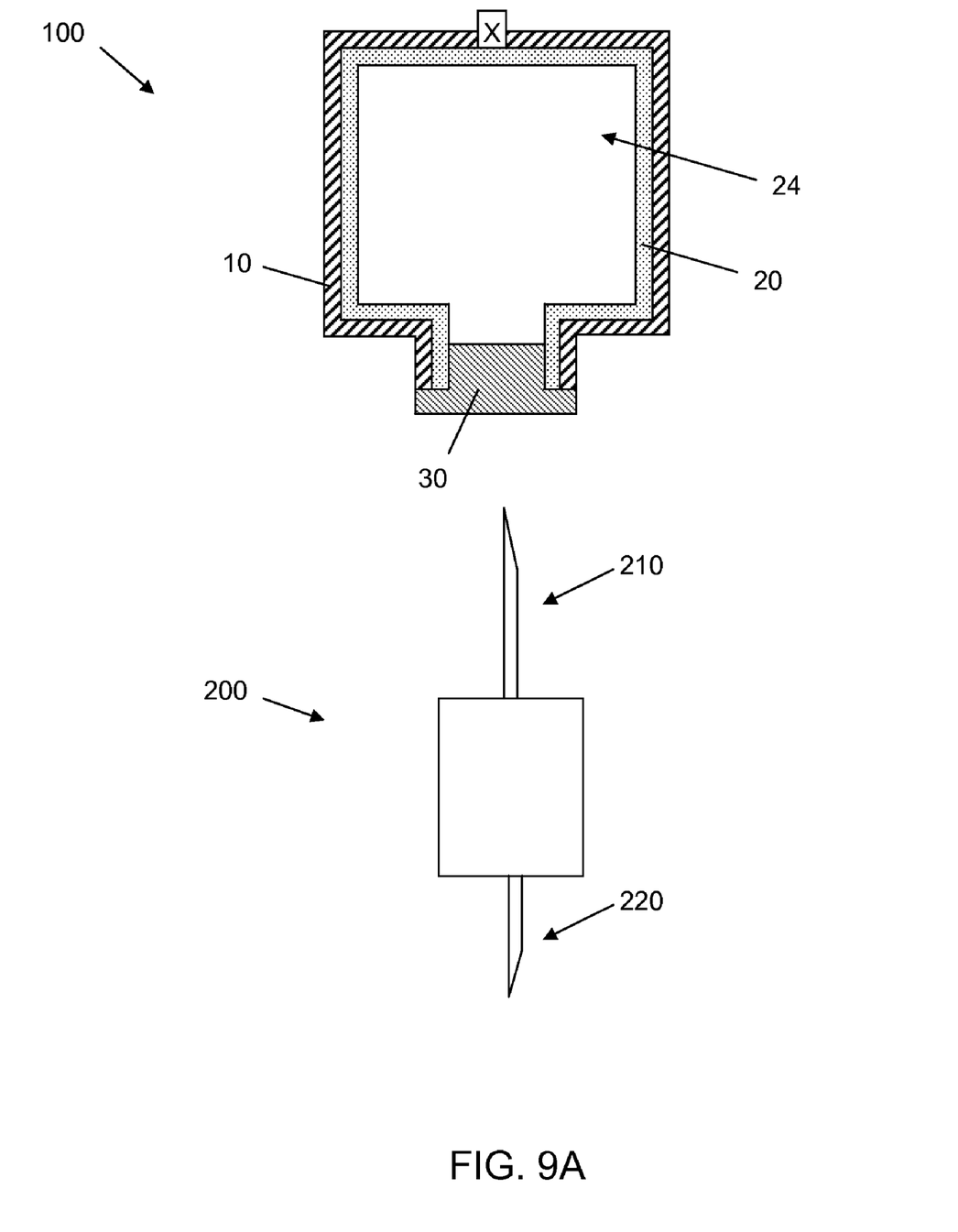
FIGS. 9A-B are schematic cross-sectional views of an embodiment of a container employed with a representative embodiment of a transdermal infusion system, which is shown in side view.
Figure 9B:
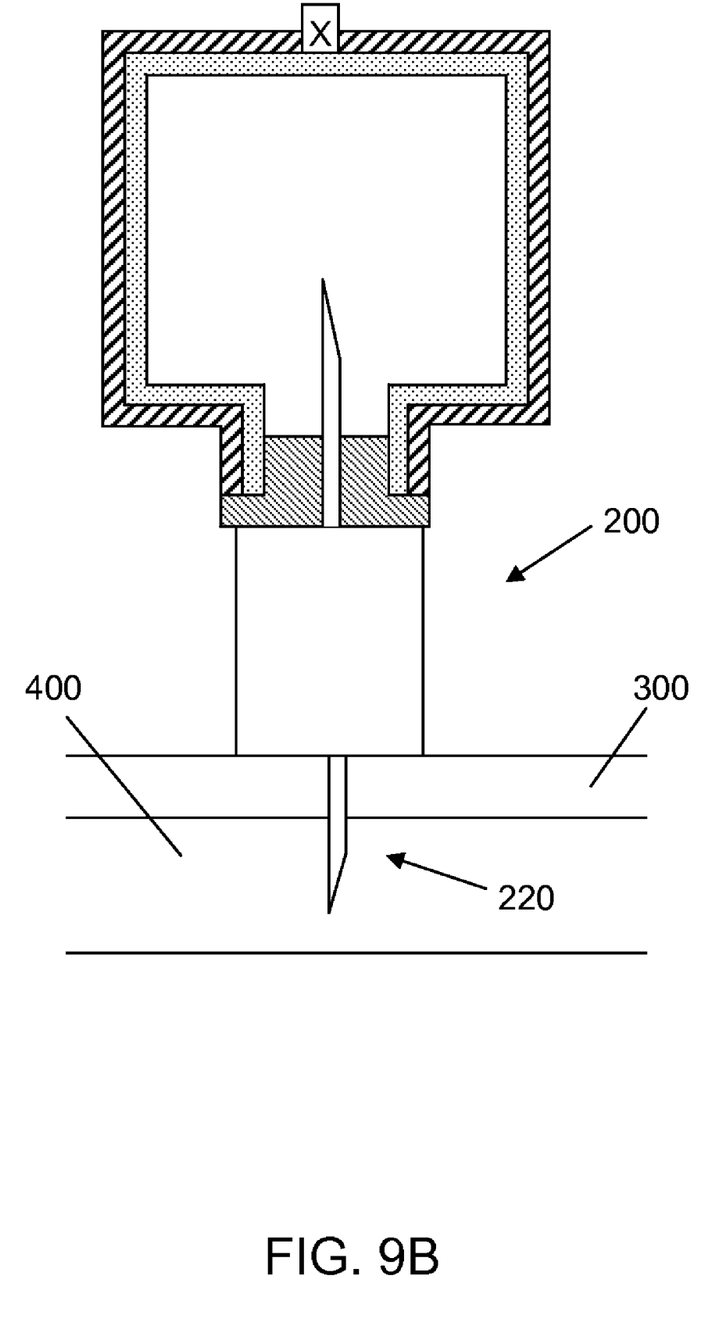
Figure 10A:
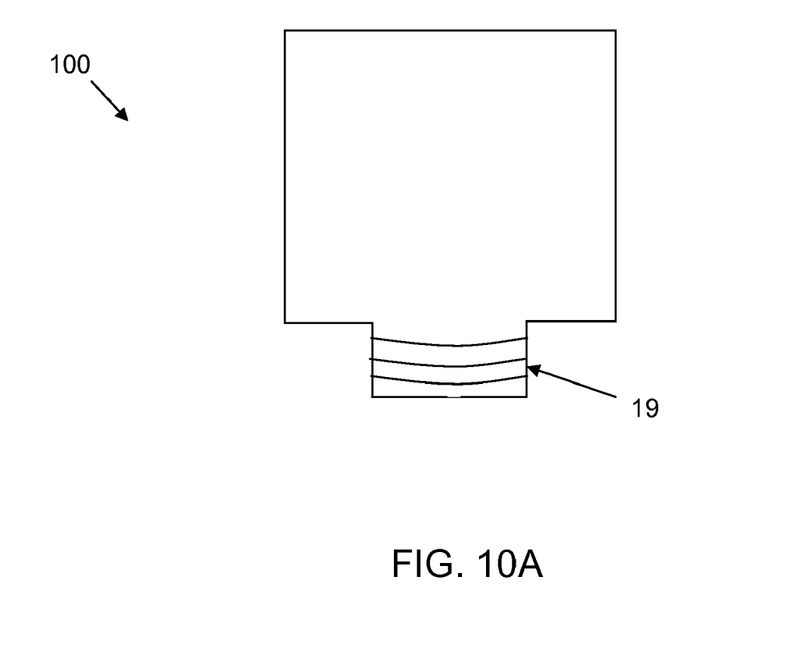
FIG. 10A is a schematic side view of a representative embodiment of a container having an externally threaded portion.
Figure 10B:
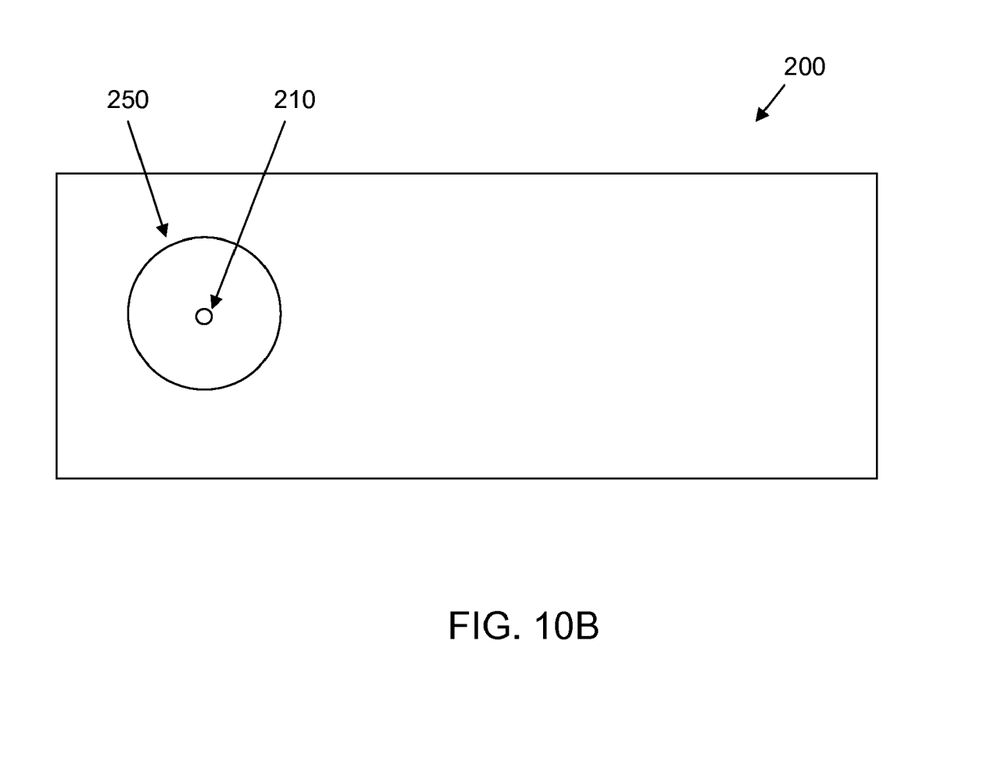
FIG. 10B is a schematic top view of a representative embodiment of an infusion system having a bore configured to receive the container depicted in FIG. 10A.
Figure 10C:
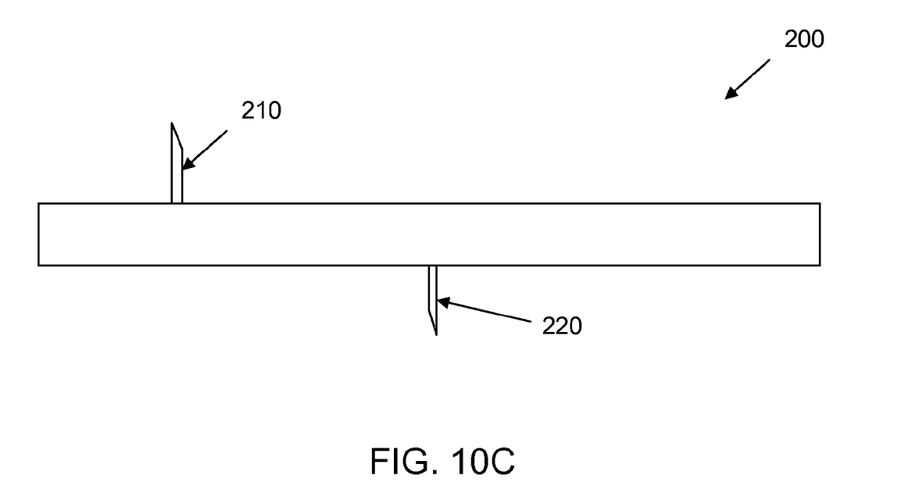
FIG. 10C is a schematic side view of a representative embodiment of an infusion system depicted in FIG. 10B.
Figure 10D:
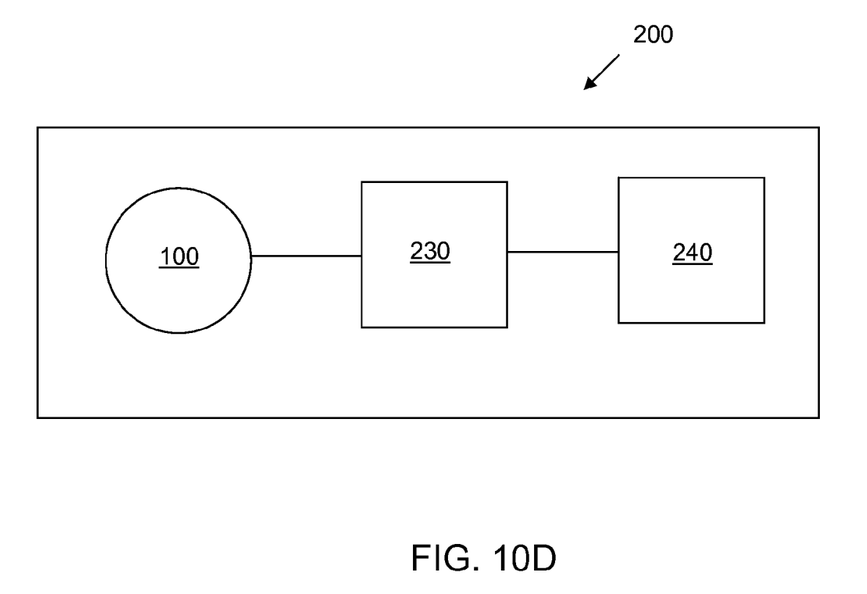
FIG. 10D is a schematic block diagram of a representative embodiment of an infusion system depicted in FIGS. 10A-B.

One suitable actuatable vent mechanism is illustrated in FIGS. 8A-B. The depicted vent mechanism 40 includes the housing 10, which contains an area of weakening 42, and includes an actuator member 45. Upon depressing the actuator member 45, the housing breaks or cracks (see FIG. 8A), creating a passageway 44 for air to flow between the inside and outside of the housing. Accordingly, the pressure inside the housing 10 can be maintained at ambient pressure, allowing fluid in the bag (not shown in FIGS. 8A-B) to be dispensed at neutral or slight positive pressure (depending on the configuration and materials of the bag). Other suitable actuatable vent mechanisms are readily identifiable by those skilled in the art. For example, a valved tube may be placed between the bag and the housing, with the valve being external to the container. One alternative to employing an actuatable vent is to evacuate air from the container prior to, or during, filling the container with therapeutic fluid.

Referring now to FIGS. 9A-B, a container 100 having a bag 20 disposed in a rigid housing 10 as described above may be incorporated into a pump system 200 for delivering therapeutic fluid housed in container to a patient. The pump system 200 includes a drive mechanism (not shown in FIG. 9), such as a peristaltic or other pump, or a flow control mechanism (not shown in FIG. 9), such as a flow restrictor. The depicted pump system 200 includes a cannula 210 capable of piercing the seal 30 of the container 100 in a fluid tight manner to place a lumen of the cannula 210 in fluid communication with the cavity 24 of the bag 20 that houses the therapeutic fluid. The depicted pump system 200 further includes a catheter 220 configured to deliver the therapeutic fluid to a target location of the patient. The cannula 210 and the catheter 220 are fluidly coupled. A drive mechanism (not shown) may be positioned fluidly between the cannula 210 and the catheter 220 to control the delivery of therapeutic fluid from the container 100 to the patient. As shown in FIG. 9B, the pump system 200 may be a transdermal pump system, such as a patch-type pump system, where a portion of the system 200 is external to the patient and the catheter 220 penetrates the patient's skin and directs flow of the therapeutic fluid to a target tissue 400 of the patient.

An example of another suitable transdermal pump system 200 with which a container 100 as described herein may be employed is depicted in FIGS. 10A-D. As shown in the schematic side view shown in FIG. 10A, a container 100 may have external threads 19 near or around the opening of the housing. As depicted in the schematic top view depicted in FIG. 10B, the pump system 200 may include an internally threaded bore 250 configured to threadingly engage and receive the container 100. A cannula 210 is axially aligned with the bore 250 and is configured to puncture a seal of the container 100 to allow therapeutic fluid stored in the container to flow through the cannula 210. As shown in the schematic side view depicted in FIG. 10C, the transdermal pump system 200 includes a catheter 220, which may be a needle or cannula, configured to puncture the skin of a patent to deliver fluid obtained via the cannula 210 to a target location of a patient. In the embodiment shown in FIG. 10D, the pump system 200 has a drive mechanism 230 disposed down stream of the cannula in fluid communication with the therapeutic fluid in the container 100 and disposed upstream of the catheter. Electronics 240 may be operably coupled to the drive mechanism to operate the drive mechanism or control the rate at which the drive mechanism 230 pumps fluid, or allows fluid to flow, to the patient.

Any suitable drive mechanism 230 may be employed. In various embodiments, the drive mechanism 230 is a peristaltic drive mechanism. One suitable infusion system employing a peristaltic pump that can be readily modified to incorporate containers, as described herein, is described in US Patent Application Publication No. 2007/0106218, entitled "Systems and Methods for Sustained Medical Infusion and Devices Related Thereto", naming Yodfat et al. as inventors, and published on May 10, 2007.

In some embodiments, the bag of the container is biased in the empty position and therapeutic fluid is forced out of the bag due to the resilient nature of the bag. In such cases and with reference to FIG. 11, a flow restrictor 260 may be fluidly disposed between the cannula 210 and the catheter 220.

Of course, a container as described herein may be used with any suitable infusion system, whether transdermal, implantable, or the like. One of skill in the art will understand that components or steps described herein regarding a given embodiment or set of embodiments may readily be omitted, substituted, or added from, with, or to components or steps of other embodiments or sets of embodiments, as appropriate or desirable.

Thus, embodiments of PUMP SYSTEM AND CONTAINER are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A container for housing a therapeutic fluid, the container comprising:
   a housing having an opening and an interior surface, the interior surface forming a cavity having a volume;
   a collapsible bag for containing the therapeutic fluid, wherein the bag is disposed in the housing and expandable to contact the entire interior surface of the housing, wherein the bag has an opening to allow the therapeutic fluid to be introduced into, or exit from, the bag, and wherein the opening of the bag is fixed in proximity to the opening of the housing; and
   a seal configured to prevent air from entering the bag via the bag opening and to prevent air from entering the cavity of the housing via the housing opening,
   wherein the housing comprises an actuatable vent apparatus configured to allow air to flow between the outside of the housing and the cavity of the housing, when actuated,
   wherein the housing is formed from glass and the actuatable vent apparatus comprises a depressable actuator member configured to cause a crack in the glass housing to form a passageway extending from the cavity of the housing to the exterior of the housing, when depressed.

2. A container according to claim 1, wherein the seal comprises a metallic foil layer disposed across the housing opening.

3. A container according to claim 1, wherein the seal comprises a pierceable and resealable septum configured to allow fluid to be introduced into, or withdrawn from, the bag.

4. A container according to claim 1, wherein at least a portion of the seal extends into the bag opening and presses the bag against the interior surface of the housing to fix the bag relative to the housing.

5. A container according to claim 1, wherein the bag is expandable to an unstressed state having a volume that is equal to or greater than the volume of the cavity of the housing.

6. A system comprising:
a container according to claim 1; and
a pumping mechanism operably couplable to the container and configured to pump therapeutic fluid disposed in the bag out of the bag.

7. A system according to claim 6, further comprising a catheter fluidly couplable to the pumping mechanism and configured to deliver the pumped therapeutic fluid to a target location.

8. A system according to claim 7, further comprising a cannula having a lumen for transporting the therapeutic fluid, the cannula being configured to pierce the seal and being operably couplable to the pumping mechanism to allow the lumen to transport the fluid from the bag to the pumping mechanism.

9. A system according to claim 6, wherein the pumping mechanism is a peristaltic pumping mechanism.

10. A system comprising:
a container according to claim 1; and
a flow restrictor operably couplable to the bag and configured to control the rate at which the therapeutic fluid exits the bag.

11. A system according to claim 10, further comprising a cannula having a lumen for transporting the therapeutic fluid, the cannula being configured to pierce the seal and being operably couplable to the flow restrictor to allow the lumen to transport the fluid from the bag to the flow restrictor.

12. A method for delivering therapeutic fluid to a patient, comprising:
piercing the seal of a container according to claim 1 to allow access to the therapeutic fluid in the bag; and
pumping the therapeutic fluid from the bag to a target location of the patient.

13. A method according to claim 12, further comprising venting the housing of the container to allow air to flow from outside the housing to the housing cavity.

* * * * *